US009023292B2

(12) United States Patent
Rostaing et al.

(10) Patent No.: US 9,023,292 B2
(45) Date of Patent: May 5, 2015

(54) BLOOD SAMPLING DEVICE COMPRISING AT LEAST ONE FILTER

(75) Inventors: Hervé Rostaing, Le Versoud (FR); Christine Peponnet, Seyssinet (FR); Patrick Pouteau, Meylan (FR); Elodie Sollier, Gagna (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 1089 days.

(21) Appl. No.: 12/740,920

(22) PCT Filed: Sep. 26, 2008

(86) PCT No.: PCT/FR2008/001341
§ 371 (c)(1),
(2), (4) Date: Aug. 10, 2010

(87) PCT Pub. No.: WO2009/071775
PCT Pub. Date: Jun. 11, 2009

(65) Prior Publication Data
US 2010/0324449 A1 Dec. 23, 2010

(30) Foreign Application Priority Data

Nov. 2, 2007 (FR) ...................................... 07 07709

(51) Int. Cl.
*A61B 5/151* (2006.01)
*G01N 33/49* (2006.01)
*A61B 5/15* (2006.01)

(52) U.S. Cl.
CPC ............ *G01N 33/491* (2013.01); *A61B 5/1411* (2013.01)

(58) Field of Classification Search
CPC ............................ G01N 33/491; A61B 5/1411
USPC .......... 422/501, 513; 600/573, 575–579, 583; 606/159, 181, 184, 185; 604/6.15, 604/6.16, 22
See application file for complete search history.

(56) References Cited

U.S. PATENT DOCUMENTS 5,163,442 A * 11/1992 Ono ................................ 600/573
5,306,623 A    4/1994 Kiser et al.
5,364,533 A * 11/1994 Ogura et al. ................... 210/645

(Continued)

FOREIGN PATENT DOCUMENTS

| EP | 0 336 483 | 10/1989 |
| EP | 0 633 808 B1 | 11/1996 |
| EP | 1 659 404 | 5/2006 |
| JP | 2007-006973 | 1/2007 |

OTHER PUBLICATIONS

English translation for EP1659404.*

(Continued)

*Primary Examiner* — Shogo Sasaki
(74) *Attorney, Agent, or Firm* — Alston & Bird LLP

(57) ABSTRACT

Disclosed herein is a device for sampling blood by capillarity for separating a plasma phase of the blood from the cell phase. The device is a strip and includes a filter having a membrane with no clumping agents, a prefilter for spreading blood over the surface of the membrane; and an absorbent paper downstream from the filter. The membrane is dimensioned to cover only a part of the surface of the prefilter and the migration of blood by capillarity within the prefilter takes place essentially lengthwise relative to the strip before blood comes into contact with the membrane.

10 Claims, 4 Drawing Sheets

(56) References Cited

U.S. PATENT DOCUMENTS

| | | |
|---|---|---|
| 5,558,834 A | 9/1996 | Chu et al. |
| 6,106,732 A | 8/2000 | Johnston et al. |
| 2001/0011167 A1* | 8/2001 | Bouchard et al. ........ 604/385.05 |
| 2002/0007161 A1* | 1/2002 | Bouchard et al. ............ 604/354 |
| 2005/0038357 A1* | 2/2005 | Hartstein et al. ............. 600/583 |
| 2006/0030790 A1* | 2/2006 | Braig et al. .................. 600/584 |

OTHER PUBLICATIONS

International Preliminary Report for Application No. PCT/FR2008/001341; dated Jun. 1, 2010.

International Search Report and Written Opinion for Application No. PCT/FR2008/001341; dated May 8, 2009.

* cited by examiner

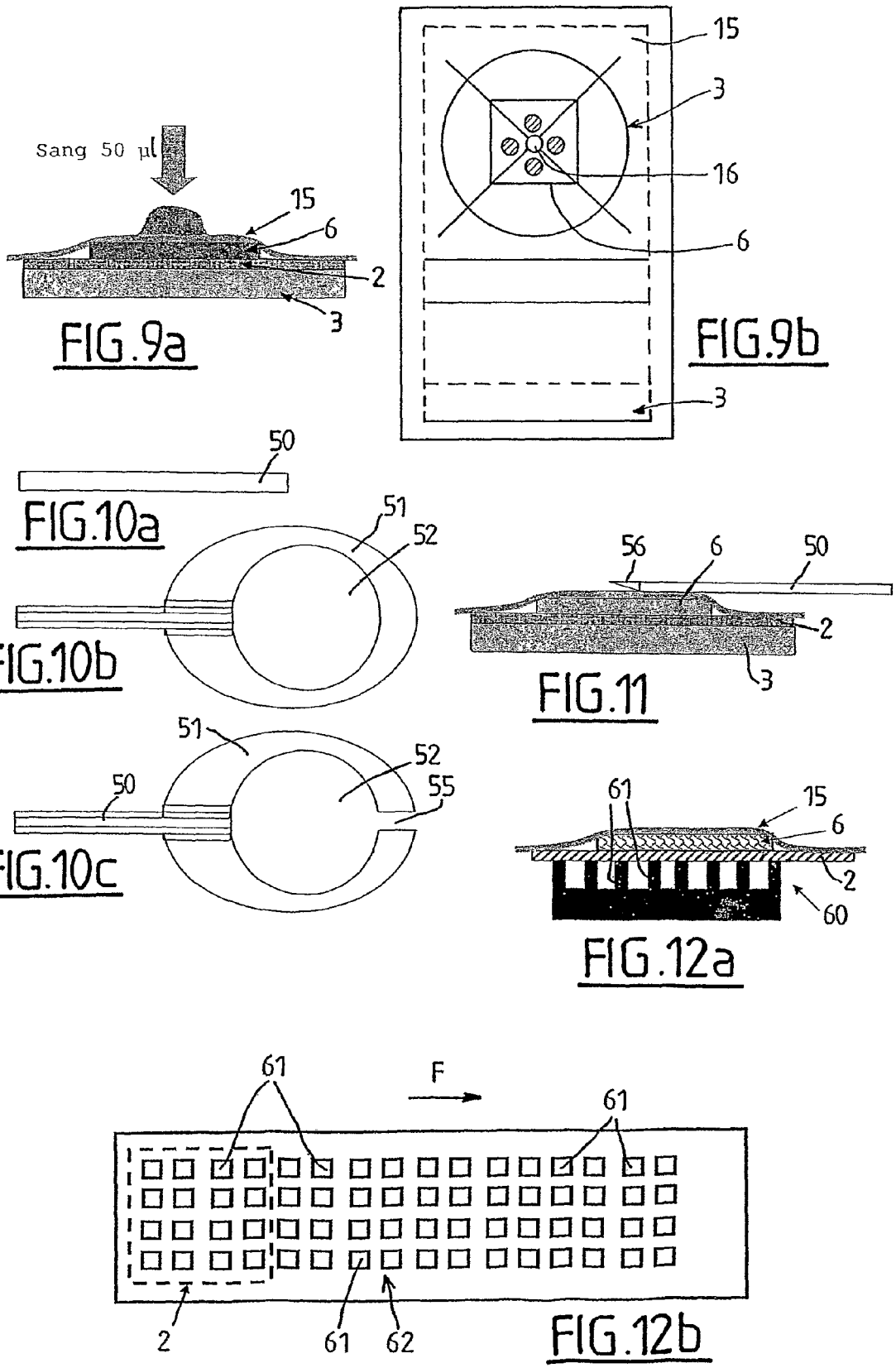

BLOOD SAMPLING DEVICE COMPRISING AT LEAST ONE FILTER

FIELD OF THE INVENTION

The invention relates to a device for taking a sample of blood for diagnosis purposes and it incorporates at least one filter for separating a plasma phase of the blood from a cell phase.

BACKGROUND OF THE INVENTION

Diagnosis devices already exist that are "exported" to a patient's home, i.e. away from care centers. Such devices need to be simple to use, and the self-taken sample needs to be measured on site or stabilized so as to be stored for several days in order to enable it to be sent (by post) to a care center for measurement purposes.

That procedure is increasing because it avoids the need for patients to travel and it enables a greater number of tests to be performed, which tests are often non-invasive and almost non-traumatic. One of the best examples is glucose testing for diabetes, which is managed completely by the patient on the basis of 1 microliter (µL) of blood.

The invention relates more particularly, but not exclusively, to a device for taking blood in order to determine the protein composition of a blood sample, in particular in the context of epidemiological studies or searching for biomarkers.

For this purpose, the blood needs to be fractioned into a plasma phase containing the proteins and a cell phase. In this application, the cells, and mainly red corpuscles, must be excluded but without being lysed in order to avoid disturbing measurement of the protein spectrum as performed using a mass spectrometer.

It is not possible to incorporate a spectrometer in a discardable device, so when the patient is not present close to the spectrometer it is necessary to stabilize the plasma for the time it takes to be transported to the measurement center, which time is generally several days. For this purpose, the plasma is preferably absorbed and dried on a specific medium.

In general, nearly all fragmentation techniques, whether for transfusion purposes, or for analysis purposes, rely on the principle of centrifuging blood. Blood cells present density that is slightly greater than that of plasma and can therefore be separated easily and effectively using conventional centrifuging techniques.

Nevertheless, that technique requires dedicated equipment and qualified personnel in order to take the blood sample and treat it. Premises for taking samples and for analyzing them are often far apart and samples often wait for many hours before they can be analyzed. During this latency time, the constituent elements of the blood (including its proteins) degrade progressively.

Furthermore, present sample-taking and fragmentation techniques are designed for treating several hundred milliliters (mL), whereas most tests require only a few hundred µL. Extracting several mL of blood is traumatic for some patients, and must not be repeated too often.

Various prior art devices exist that are suitable for separating blood cells using sample volumes that are limited to a few hundreds of microliters of blood.

In such devices, separation is performed by filters made of fiber materials, namely glass fibers, as described in U.S. Pat. No. 5,364,533 (Sanwa Kagaku Kewkyusho) for collecting a volume of blood equal to about 1 milliliter, or as described in patent application EP-0-633 808 (Gostechnology) where the glass fibers are in the compressed state.

It is also known to make use of a clumping agent or an agglutinizing agent as a separating agent. This is described as being optional in above-mentioned U.S. Pat. No. 5,364,533 and essential in U.S. Pat. No. 5,558,834 (Bayer Corp.) and U.S. Pat. No. 6,106,732 (Binax Services).

Those techniques present the following drawbacks.

Firstly, agglutinizing agents present varying selectively depending on protein type, thereby creating bias in terms of the representativity of the sample treated in that way.

Furthermore, fibers, and in particular glass fibers, do not retain all corpuscles, thereby disturbing mass spectrometer measurement in which it is important to use plasma that is very clear, i.e. without any hemoglobin from red corpuscles.

SUMMARY OF THE INVENTION

The invention thus provides a device for sampling blood by capillarity, the device incorporating a filter and, downstream therefrom, an absorbent material for separating a plasma phase of the blood from a cell phase, the device being characterized in that the filter comprises in succession:
  a prefilter (6) for spreading the blood over the surface of a first membrane (2) having pores of dimension lying in the range 0.1 micrometers (µm) to 5 µm, said membrane having no clumping agent; and
  said first membrane (2).

The blood collection device may be incorporated in a diagnosis device or it may be separate therefrom.

The size of the pores advantageously lies in the range 0.5 µm to 5 µm in order to avoid lysing the corpuscles. The density of the pores may be such that they occupy 10% to 90%, and more particularly 40% to 80%, and preferably 50% to 80% of the surface area of the membrane.

At least one second membrane having pores of the same size and/or the same pore density or having pores of a different size and/or a different pore density may be superposed on the first. Upstream from the first membrane, relative to the direction blood flows through the filter while a sample is being taken, the device may present an absorbent and/or filter paper serving to spread the blood over the surface of the filter, said paper possibly including fibers, and in particular glass fibers that perform partial filtering of the cell phase.

In a variant, it is particularly advantageous to place an absorbent paper downstream from the membrane(s) of the filter, which paper is suitable, after drying, for conserving proteins.

The absorbent paper may present precut lines enabling aliquots to be separated. The section of the absorbent paper is preferably greater than that of the filter, and under such circumstances it may present, outside the outline of the filter, handling zones that are suitable for being touched without risk of contaminating the sample that has been taken.

The outline of the absorbent paper may be structured by marking (ink or adhesive impregnated in its thickness) or it may be compressed so as to facilitate good spreading of the collected plasma phase.

In another variant, instead of absorbent paper, the device presents a region that is structured as an array, e.g. an array of pillars, in particular made of plastics material or of silicon, for retaining the plasma phase by capillarity. The array may also propagate the filtered liquid by capillarity towards an analysis or stabilization zone.

The blood collection device advantageously presents at least one needle of length L, e.g. lying in the range 200 µm to 2 millimeters (mm), and preferably in the range 1 mm to 2 mm, and adapted to taking blood from the dermis.

The collection device may include a matrix of needles of length L arranged over the surface of the filter, thereby enabling the collected blood to be spread over the filter.

The device may include an anticoagulant in lyophilized, dry, or moist form covering the walls of the collection device that come into contact with the blood and/or at least one wall of the filter.

The device may be housed in a housing that includes an evacuated enclosure, downstream from the filter. The collection device may include a protective film that covers the needle(s) of the sample-taking device so as to maintain the vacuum under such circumstances.

The device may include a prefilter of volume that is dimensioned so that the absorbent paper will always be saturated in plasma.

The device, in the form of a strip, may comprise a strip support for stiffening the device as a whole, e.g. a support that is of hydrophobic and non-absorbent nature.

The device may be arranged in such a manner that the end of the prefilter projects from the remainder of the device, e.g. by about 1 mm.

BRIEF DESCRIPTION OF THE DRAWINGS

The invention can be better understood on reading the following description with reference to the drawings, in which:

FIGS. 9a and 9b are respectively a section view and a plan view of another embodiment of the device of the invention;

FIGS. 10a to 10c show separate collection means operating by capillarity suitable for use with the sample-taking device of FIGS. 9a and 9b, with FIG. 11 showing collection means incorporated in the device of FIGS. 9a and 9b;

FIGS. 12a and 12b show a variant presenting an array of pillars arranged to enable the plasma phase to be collected by capillarity.

DETAILED DESCRIPTION OF THE INVENTION

Figure 1:
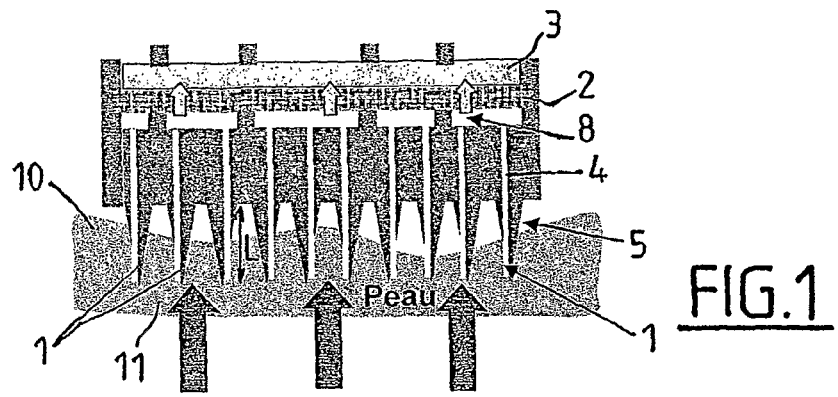
FIG. 1 shows an embodiment of the invention with an incorporated collection device presenting a matrix of needles.

The device described below with reference to FIGS. 1 and 2 serves to separate total blood into a cell fraction and a plasma fraction. More precisely, blood cells are retained by a filter 2 by dimensional segregation and without using any clumping agent of the lectin or agglutinin type in the device, with the plasma passing through the filter and then being stored in absorbent means 3.

The structure is for the most part "vertical" (a stack of layers) and comprises a blood-collection portion (which is optionally incorporated in the device), optional suction means (FIG. 2) for sucking blood, optional spreader means for spreading blood over the filter, a filter element, absorption means for absorbing plasma without denaturing proteins, and removal and drying means for removing and drying the absorbed plasma. These storage means may be detachable. The spreader means may be incorporated in the collection portion that is constituted for example by a matrix of needles, or in the filter portion in the form of a prefilter.

The dried plasma is analyzed subsequently (up to several weeks later). For example, it is sent by mail for protein content to be measured by mass spectrometry.

The device described is constituted firstly by a needle or a matrix of needles 1 having the function of piercing the epidermis in order to collect a drop of blood (10 µL to 150 µL) from the dermis. The needle 1 may have an optimum depth for limiting the jabbing sensation while taking the sample. Typically, needle length could lie in the range 200 µm to 2 mm and its diameter is preferably less than 2 mm. The needles 1 may be hollow in order to collect blood directly from the core of the dermis.

A matrix of needles 1 is advantageous for spreading the blood uniformly over the filter as explained below in the description, and also for reducing the sensation of pain by shortening the length L of the needles. Each needle needs to take less blood, and therefore the depth to which it needs to penetrate into the dermis is less.

The insides 4 of the needles 1 and/or of the chamber 8 at the surface of the filter and/or the prefilter 6 that spreads the blood may be prefilled with an anticoagulation agent and/or with a lyophilized anti-hemolysis agent.

Figure 2:
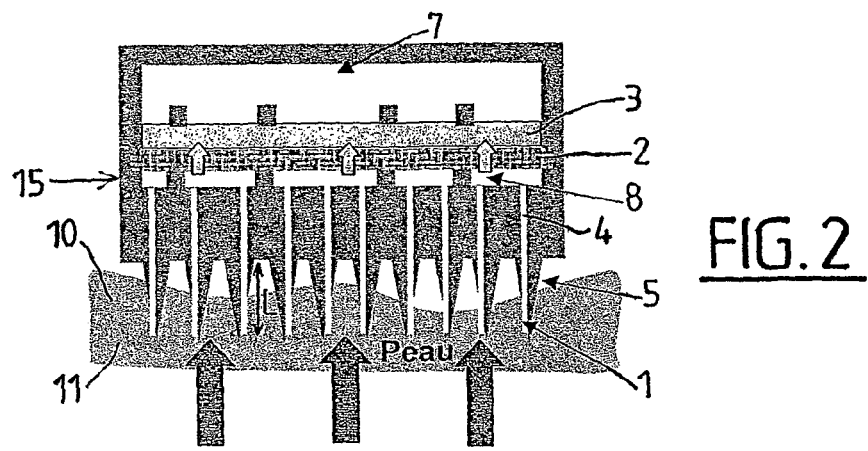
FIG. 2 shows the FIG. 1 device in a housing with an optional vacuum enclosure.

The diffusion of blood towards the inside of the device may be ensured by means of the donor's blood pressure, by means of capillarity forces generated by microstructuring various component parts of the device (e.g. making them porous), or indeed by applying suction in a portion of the device (cavity 7 in FIG. 2). In terms of lysis and cleanness of the sample, it is clearly advantageous to take the blood directly from within the skin (at a depth of approximately 1 mm) while avoiding any contact with the surface.

The taking and filtering system may be included in a system for taking hold of the finger (like a clothes peg) in order to hold the needle(s) and the system in place while blood is being taken and in order to take blood by more quickly squeezing the patient's finger.

The blood is put into contact with one or more filter membranes 2 constituting the filter. The main membrane may be a commercially-available filter of any type, and it preferably has pores in the range 0.1 µm to 5 µm and is preferably a pierced membrane that is fine (thickness lying in the range 1 µm to 100 µm) and with holes at a density that is as high as possible. In addition, the main filter 2 is not a glass fiber filter nor a cellulose filter because of defects due to the presence of filtering by fibers. As explained below, a glass fiber filter may however be used upstream from the membrane as a prefilter 6 for spreading the blood over the membrane and for prefiltering corpuscles. The filter portion 2 may be a superposition of pore filters and/or of different structures, but it should never have a clumping or agglutinating agent.

This portion is preferably compressed or bonded against means that absorb plasma in order to maximize the force of capillarity that sucks the plasma through the membrane. Pore density may be maximized in order to obtain the greatest possible quantity of filtered plasma before the filter saturates.

The collected blood is advantageously spread uniformly over the surface of the filter. This function is provided by:
- the needles 1 being organized as a matrix, thereby ensuring that blood is supplied uniformly over the area; and/or
- a fiber structure prefilter 6 that saturates with blood by capillarity and that therefore spreads the drop of blood over the entire surface of the filter. This prefilter may thus assist in prefiltering the blood before the much finer filtering of the filter; and/or
- prefilling an empty space corresponding to the volume of blood that is to be treated (10 μl to 150 μL, and preferably 50 μL) by capillarity on its walls (FIGS. 12*a* and 12*b*); and/or
- by vacuum suction (e.g. cavity 7, FIG. 2), thereby enabling the blood to be spread directly over the entire membrane; and/or
- by manual spreading using a calibrated capillary.

The filtered plasma is then absorbed by storage means, namely a hydrophilic substrate on which the plasma spreads out, such as the "Whatman Protein Saver 903" paper from the supplier Whatman, or indeed a capillary force creating structure such as an array of pillars. This portion of the device has the property of being capable of being separated from the remainder of the device. Advantageously, the storage means are of defined volume so as to enable the volume of the collected plasma sample to be calibrated accurately.

Various techniques can be envisaged for drying and conserving the sample. Drying may be in open air, in a vacuum, by lyophilization, . . . . Conservation may be in an individual sachet or in a container with an antimoisture agent (such as a desiccating sachet), or in a container that may also be evacuated of air for the purpose of enhancing protein conservation.

Tests have been performed with a stack (see FIGS. 9*a* and 9*b*) made up of a prefilter 6 made of glass fibers (pore size 3 μm, thickness in the range 100 μm to 400 μm), a membrane 2 presenting holes with a diameter of 1 μm (porosity lying in the range 20% to 50%), and adhesive paper 15 compressing the filter portion 2 against the absorbent means 3 (Protein Saver 903 paper).

50 μL of non-diluted total human blood protected against coagulation by EDTA (hematocrit: 45%) is placed on the device. The membrane is held manually in contact with the absorbent paper during filtering. A quantity of plasma lying in the range 7 μL to 11 μL is filtered in a few minutes in the absorbent paper 3.

FIGS. 1 and 2 show an embodiment of the invention, in which the following can be observed:
- The collection means (needle) are incorporated in the device and present dimensions that are adapted to the volume of blood that is to be taken (50 μL).
- The use of a filter membrane 2 operating by porosity without any clumping agent and optionally coupled with a prefilter for filtering the blood.
- Means for calibrating the quantity of filtered blood (prefilter, chamber 8 of given volume).
- The use of an absorbent paper 3 that is not destructive for proteins in order to recover the plasma by capillarity through the filter 2. This paper may be precut (FIG. 7) so as to make it easier to aliquot and structure it in order to confine the plasma in a predefined zone.

Figure 4:
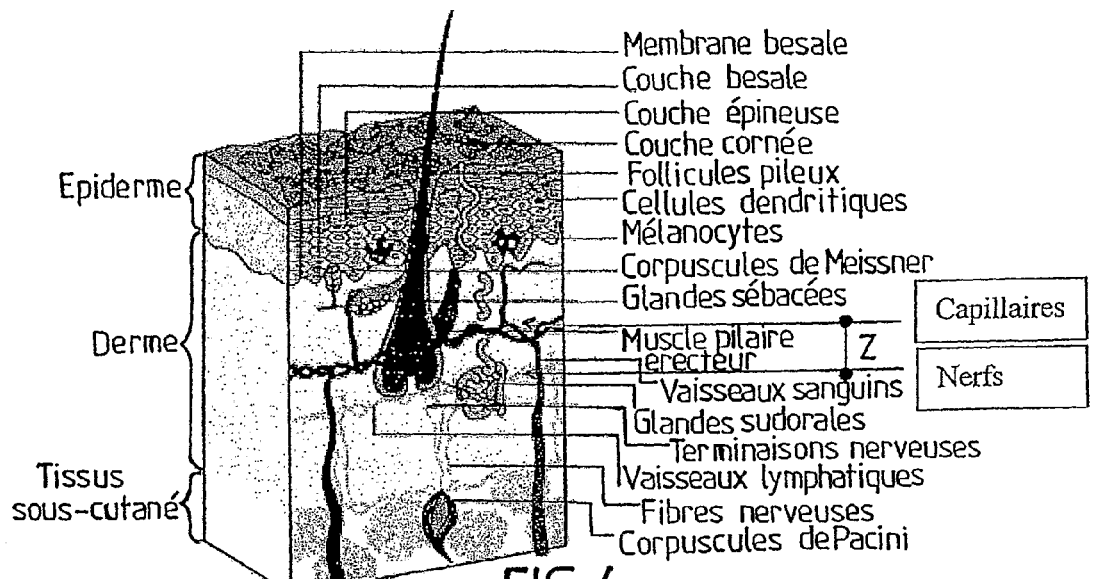
FIG. 4 is a section view showing the zone of the dermis that is relevant for taking a sample painlessly.

In the example of FIGS. 1 and 2, the surface of the device is made up of a matrix of needles 1 (a few needles to more than one hundred) having a length exceeding L such that the needles pierce the epidermis 10 but do not penetrate deeply into the dermis 11 so as to be capable of taking blood while greatly limiting the patient's sensation of pain (200 μm to 2 mm). FIG. 4 shows the pertinent zone Z of the dermis (level with capillaries and upstream from nerves). In this way, coagulation at the surface of the finger is very fast and leaves less of a mark than does standard sample-taking.

Figure 6:
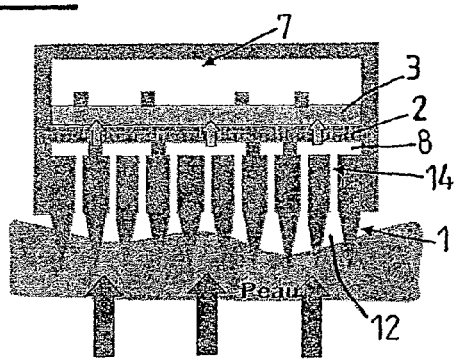
FIG. 6 shows a variant in which the needles are solid.
Figure 8A:
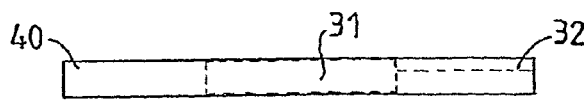
FIGS. 8a to 8d show assembly of a device of the invention.
Figure 8B:
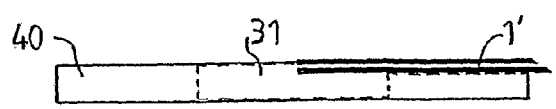
Figure 8C:
Figure 8D:
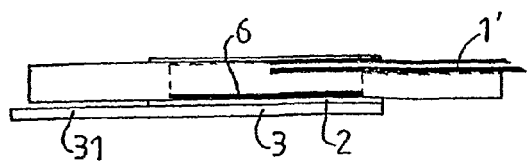

The needles 1 may be solid or hollow. If they are hollow, blood is collected directly from the core of the dermis, thereby presenting a clear advantage in terms of the quality of the blood. If they are not hollow, then holes 12 are present at the bases of the needles, as shown in FIG. 6, to channel the blood within the device through a channel 14 towards a cavity 8 adjacent to the filter 2.

Because the needles 1 are arranged in a matrix, blood is spread directly over the filter 2.

The needles 1 open out into a collection cavity 8.

Reference 2 designates a filter membrane possibly having a prefilter 6 upstream therefrom.

Reference 3 designates an absorbent medium, possibly suitable for peeling off.

An anticoagulant in lyophilized, dried, or moist form may be present on the walls of the channel 4 or 14 of the needles and on the upstream surface of the filter 2 in contact with the blood being taken.

A film 5 may be provided for protecting the needles 1, which film may be removed prior to utilization, or it may break as the needles 1 penetrate the skin.

FIG. 2 shows a sample-taking device like that of FIG. 1, but placed in a housing 15 that includes an evacuated volume 7.

Figure 3:
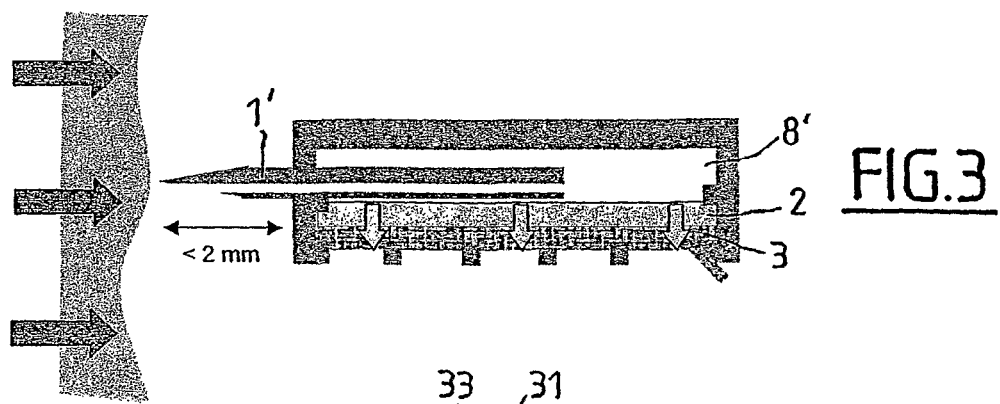
FIG. 3 shows a variant of the invention for collection using a single needle.

In the example of FIG. 3, the device is made up of a single needle 1' that may be a little longer and wider than with a matrix of needles since all of the blood needs to be taken through the single needle, and that is in communication with a cavity 8 adjacent to the filter 2.

The device remains implanted in the patient's skin throughout the time the chamber 7 or 8 is being filled. The end of filling may be determined by means of a transparent cap or by using a sample-taking time that is determined a priori (from a few seconds to a few minutes).

A second possibility is to have a device for ejecting and retracting the needle that is incorporated in the device in order to pierce a hole for taking blood, while avoiding the traumatizing aspect of keeping a needle under the skin.

In any event, it is preferable to use a prefilter 6 (e.g. a prefilter of glass fibers) upstream from the main membrane 2 in order to spread the blood uniformly over the main membrane 2. The layer constituting the prefilter is sufficiently fine to be practically saturated by the drop of blood that is to be taken, and thus to ensure that the blood is well spread over the filter 2.

Advantage is thus taken of the shape and the structure of the prefilter 6 for the purpose of spreading the blood uniformly in contact with the filter membrane 2. The corpuscles contained in the blood are preferably retained in the prefilter 6, which prefilter limits and holds said corpuscles, thereby delaying them making contact with the membrane; this may serve to avoid any risk of premature lysis of the corpuscles.

The filter membrane 2 is defined as a fine film of thickness lying in the range 0.2 μm to 100 μm, with its thickness being selected as a function of not lysing the filtered cells. By way of example, the membrane may be made of polycarbonate, of cellulose, of silicon, or indeed of silicon oxide. It has holes of diameter preferably lying in the range 0.1 μm to 5 μm, with their axes preferably perpendicular to the surface of the membrane 2. Porosity is defined herein as being a density per unit area, i.e. the ratio of the area of the holes or pores to the total surface area of the membrane (as contrasted with volume-related terms as is usually the case). It lies in the range 10% to 90%, and preferably in the range 40% to 50%.

Filter Pore Density Per Unit Area

Consider a standard filter for which it is estimated that the density of its pores (having a diameter of 1 µm) is 15 per 100 square micrometers (µm$^2$), i.e. about 12% of the surface area of the filter. The diameter of the filter is 25 mm for example, thus representing 74 million holes having a diameter of 1 µm in the filter.

Blood is made up as follows (commonly accepted data):
red corpuscles: $5 \times 10^9$/mL;
platelets: $3 \times 10^8$/mL;
white corpuscles: $3 \times 10^6$/mL.
I.e. for a 50 µL drop:
red corpuscles: $2.5 \times 10^8$;
platelets: $1.5 \times 10^7$;
white corpuscles: $0.35 \times 10^6$;
giving a total of $2.65 \times 10^8$ cells for filtering, i.e. 265 million cells.

In this example there are 3.6 times as many cells for filtering as there are pores in the filter. The filter therefore becomes clogged before all of the plasma has passed through it, unless a plurality of filters are superposed.

With a similar single-layer filter having pore density greater than or equal to 43%, i.e. 3.6 times greater, then all of the plasma can be filtered.

Figure 5:
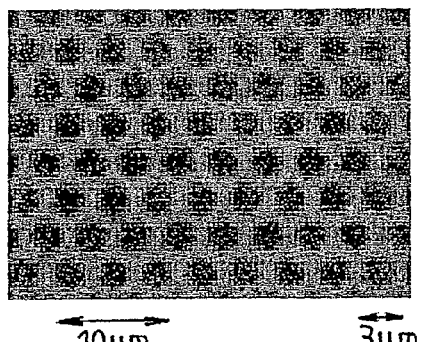
FIG. 5 shows an example of a filter membrane usable in the context of the invention.

FIG. 5 shows an example of a silicon membrane filter with high pore density (>70%), the pores presenting a diameter of 1 µm.

For the intended application, the storage means are a preferably hydrophilic substrate over which the plasma spreads (e.g. a substrate of the Whatman "Protein Saver 903" type) and it advantageously has the property of conserving proteins after drying.

The thickness of the storage means is determined as a function of the quantity of blood taken so as to enable the filtered plasma to be uniformly spread over the absorbent paper.

The absorbent paper may have a hole in the center to allow a needle to pierce the skin directly without damaging the filters and the absorbent paper.

The plasma collection means may also be a surface that is not absorbent but that is structured to receive 10 µL of plasma, e.g. an array of pillars made of plastics material or of silicon having a volume of about 10 µL and having good properties of suction by capillarity (preferably hydrophilic).

Figure 7:
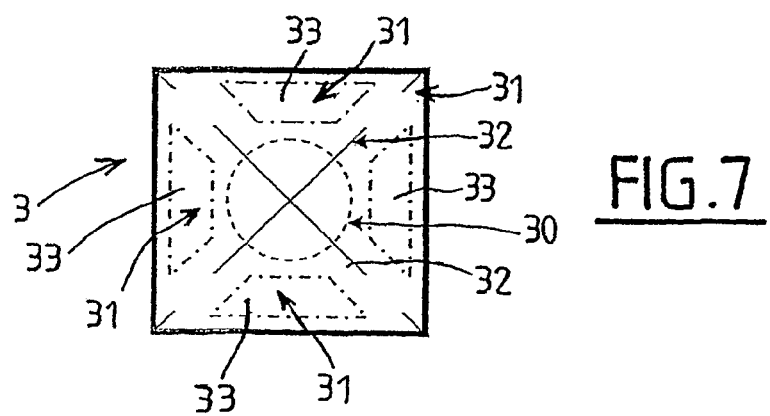
FIG. 7 shows an embodiment of absorbent paper suitable for use in the invention.

FIG. 7 shows an absorbent paper that is particularly suitable. Its section is greater than the outline 30 of the filter 2, thus making it possible to have zones 31 that may be touched without risk of contamination and that enable samples to be marked, e.g. by means of a bar code. It presents precut lines 32 enabling a plurality of samples to be separated out (aliquoting). In order to ensure that the extracted plasma can be aliquoted in simple manner, the paper is advantageously precut along lines 32 so as to enable the extracted plasma to be separated into a plurality of aliquots of comparable quantity. The papers are precut in such a manner that aliquoting is performed simply and without making contact with the portion where the plasma is absorbed and without using any special tool. The absorbent paper may also be of fairly small thickness, thereby encouraging uniform spreading of the plasma thereover, and it may have a structured surface (local compression of the paper) so as to confine and orient the spreading of the plasma. The portion of the paper for handling (outside the outline 30 of the filter 2) may also contain a sample identification zone (e.g. a bar code, a zone for writing, a radio frequency identity (RFID) strip, ...) on the front or the back of the sample.

An embodiment is described below with reference to FIG. 8.

Here the starting point is a plastics plate 40 having thickness lying in the range 1 mm to 2 mm and including a central hole 31 of diameter smaller than the diameter of the filter 2, and a groove 32 going from the center towards the edge of the device. A needle 1' is initially adhesively bonded in the groove 32. The main filter 2 is adhesively bonded under the plastics plate, and the filter paper or prefilter 6 serving for spreading the blood over the surface of the filter 2 is placed on the main filter 2. Thereafter the plasma absorbent paper 3 is adhesively bonded against the main filter 2 under the device. A protective film may also be adhesively bonded to the top of the device made in this way.

The device shown in FIGS. 9a and 9b presents a filter membrane 2 having a pore size of 1 µm and covered in a glass fiber prefilter 6 with pore size substantially equal to 3 µm that sucks up and spreads the blood over the membrane 2 while prefiltering a fraction of its cells. The assembly that also includes an absorbent paper 3 is compressed by an adhesive 15 that presents, over the prefilter 6, an opening 16 for passing blood.

Once filtering has been performed, the adhesive is peeled off.

The membrane 2 and the prefilter 6 that are stuck to the adhesive are thus removed together therewith at the end of sample-taking, so as to release the absorbent paper 3.

FIG. 10a shows a blood-collecting capillary 50 that enables a determined quantity of blood to be collected after a patient's dermis has been pierced and that is coupled with a flexible bulb 51 presenting a cavity 52 (FIG. 10b) for pipetting and expelling the drop of blood. FIG. 10c shows a variant in which the bulb 51 has a hole 55 at its end opposite from the capillary 50 for sucking up blood by capillarity and for expelling it by squeezing the bulb 51. The capillary 50 presents a volume lying in the range 50 µL to 100 µL and is preferably treated with an anticoagulant (preferably EDTA), and it is used as an intermediary. After piercing, it enables an accurate volume of blood to be collected by being filled by capillarity (i.e. in the bulb), and it enables the contents to be emptied directly on the filter device, either using the bulb 51, or as described below with reference to FIG. 11.

FIG. 11 shows a capillary 50 terminated by a lancet 56 that is incorporated in the device of FIGS. 9a and 9b. The capillary 50 fills by capillarity, and once it is full, the blood comes into contact with the prefilter 6, and the blood is sucked in by capillarity by the prefilter 6, so the capillary 50 empties progressively through the lancet 56.

The device shown in FIGS. 12a and 12b is similar to the device of FIGS. 9a and 9b except that blood is collected by an array 60 of silicon pillars 61 presenting a 50 µm×50 µm section and spaced apart by 50 µm gaps. In this example, the pillars present a depth of 200 µm.

FIG. 12b shows the filter zone 62 and the array 60 of pillars 61 for collecting plasma, which plasma propagates by capillarity in the direction of arrow F. If the pillars 61 are situated solely facing the filter 2, then the plasma is held by capillarity without the above movement.

Figure 13A:
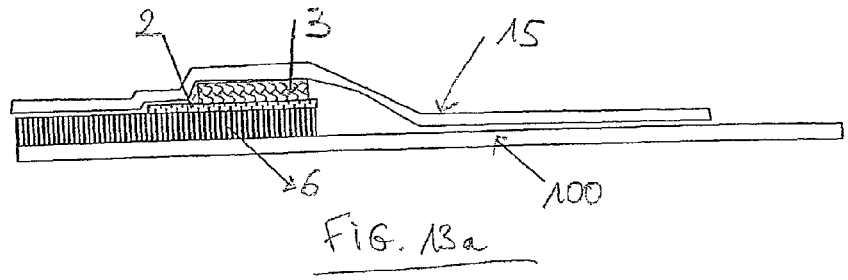
FIGS. 13a to 13c show another variant embodiment of the invention respectively in section view in FIGS. 13a and 13b, and in plan view in FIG. 13c.
Figure 13B:
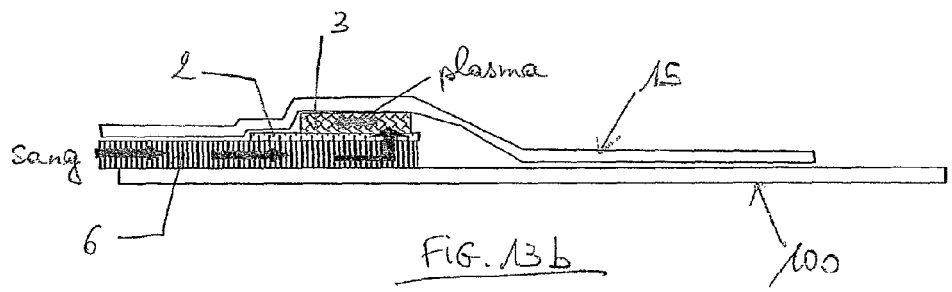
Figure 13C:
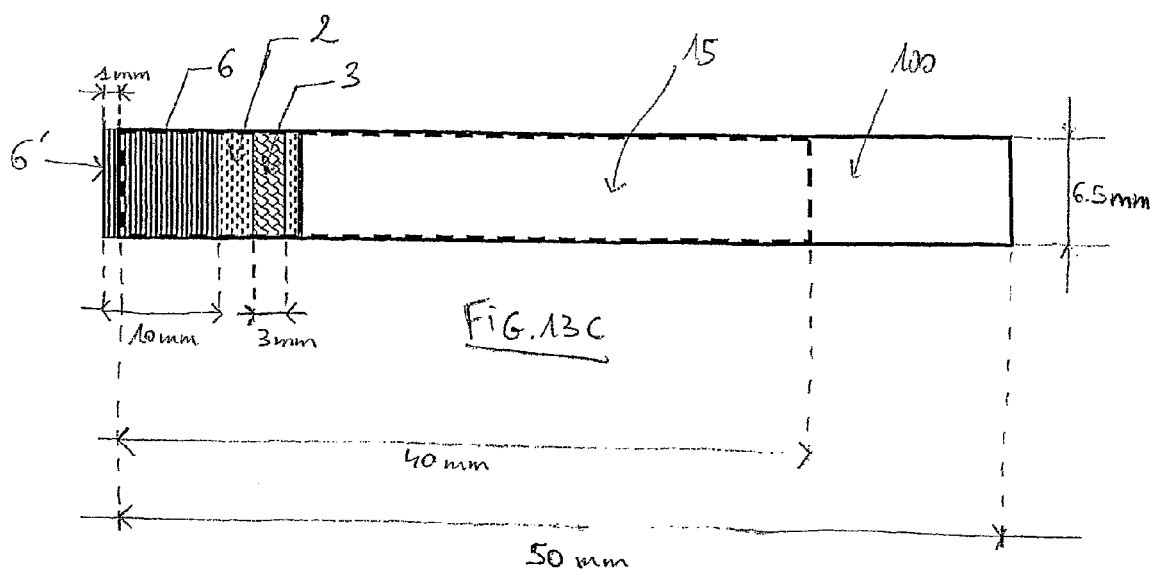

The embodiment shown in FIGS. 13a to 13c presents a device in the a form of a strip that comprises: a strip support 100; a prefilter 6 mounted on the strip support 100; a membrane 2 mounted on the prefilter 6; an absorbent paper 3 mounted on the membrane 2; and a peel-off adhesive 15 in contact with the absorbent paper.

The prefilter 6 is for collecting blood from the capillary puncture, via its end 6'. The end 6' of the prefilter projects a little beyond the remainder of the strip, e.g. by about 1 mm.

The volume of the prefilter 6 enables it to collect a quantity of blood that is sufficient to enable blood cells to be filtered, with optimum filling of the absorbent paper 3 with plasma. By way of example, it is possible to envisage the prefilter 6 being a Whatman Fusion 5.

The filter membrane 2 forming a barrier to blood cells that have not been filtered is constituted, for example, by a GE membrane with pores having a diameter of 1 µm (pore diameter is always selected so that the plasma can flow easily and so that the capillary force of the absorbent paper 3 does not lyse the cells against the pores of the membrane).

The absorbent paper 3 presents dimensions that are selected to become saturated with a certain volume of plasma, typically lying in the range 5 µL to 6 µl. By way of example, it may be constituted by Whatman Protein Saver 903.

The absorbent paper 3 is secured to the adhesive 15 that is peeled off after filtering, in a manner analogous to certain other embodiments of the invention. The other face of the adhesive 15 may include a surface that is printable, e.g. in order to enable a bar code to be applied thereto so as to ensure traceability of the sample of blood that has been taken. It is also possible to provide for said other face of the adhesive to be made of or to include a coating that becomes colored in contact with plasma, so that the user can be sure that the device has operated properly.

The strip support 100 enables the device as a whole to be stiffened, and may for example be made of card, e.g. of the Bristol board type; and it is advantageously a material that is hydrophobic and not absorbent, in contrast to the filters and the prefilter.

The prefilter 6 is dimensioned so that the absorbent paper 3 always saturates with plasma so as to guarantee a constant volume of plasma is collected, regardless of the patient (the quantity of hematocrit or the viscosity of blood may vary from one patient to another).

It can also be understood that the materials are selected so that the adhesive 15 can be peeled off without tearing away the various layers of the stack (support, prefilter, membrane, absorbent paper).

The device may present width lying in the range 5 mm to 7 mm: this width thus corresponds to the width of all of the elements of the device. In contrast, the various elements may be of differing length as a function of requirements (volume of blood to be taken, volume of plasma for aliquoting).

For example, the device shown in these figures enables 40 µL of blood to be taken (with a prefilter having a width of 6.5 mm and a length of 10 mm), and to collect 5.6 µL of plasma (with absorbent paper 3 presenting a width of 6.5 mm and a length of 3 mm). These dimensions are marked in FIG. 13c and the adhesive 15 and the support 100 presents different dimensions (namely 40 mm and 50 mm).

The operation of the device is shown more particularly in FIG. 13b.

The device shown takes advantage of prior retention forming in the prefilter: since blood arrives via the edge face 6', it comes into contact with the membrane 2 only after a capillarity migration time, the membrane 2 being dimensioned to cover only part of the surface of the prefilter 6. Thus, the constituents of the blood move at different speeds in the prefilter 6 (proteins move faster than corpuscles), thereby enhancing filtration and segregation of the constituents of the blood.

In other words, the migration of blood by capillarity within the prefilter 6 takes place essentially lengthwise relative to the strip, and advantage is taken of this migration time to filter in advance the arrival of the blood constituents on the membrane 2, thereby preventing any risk of said membrane saturating.

The patient begins by piercing a finger with a lancet and then applies the end 6' of the prefilter 6, which end projects a little from the remainder of the device. The prefilter 6 fills with blood by capillarity. Once the prefilter 6 is full of blood, the absorbent paper 3 is observed to become wet, where wetting also takes place by capillarity. The device shown in FIGS. 13a to 13c is thus arranged so that blood travels upwards (relative to gravity) and by capillarity.

Once the sample has been taken, it is necessary to wait for about 2 minutes before peeling off the adhesive portion.

The invention claimed is:

1. A device for sampling blood by capillarity for separating a plasma phase of the blood from a cell phase, wherein said device is in the form of a strip that comprises:
   a filter comprising:
      a membrane having pores of dimension lying in the range 0.1 µm to 5 µm, said membrane having no clumping agent; and
      a prefilter, on which said membrane is mounted, for spreading the blood over a surface of said membrane;
      said membrane being further dimensioned so as to have a contact surface with the prefilter that covers only part of a surface of said prefilter, so as to ensure that the migration of blood by capillarity within said prefilter, between an edge face of said prefilter and the contact surface of the membrane with the prefilter, takes place essentially lengthwise relative to the prefilter before blood comes into contact with said membrane, wherein the membrane does not cover the edge face; and
   an absorbent paper mounted on the membrane.

2. A device according to claim 1, wherein the dimension of the pores lies in the range 0.5 µm to 5 µm.

3. A device according to claim 1, wherein the density of the pores is such that said pores occupy 10% to 90% of the surface area of the membrane of the filter.

4. A device according to claim 3, wherein the density of the pores is such that said pores occupy 40% to 80% of the surface area of the membrane.

5. A device according to claim 1, wherein said prefilter is an absorbent or filtering paper that includes fiber.

6. A device according to claim 1, wherein said device includes a stiff support on which the prefilter is mounted.

7. A device according to claim 1, wherein the device includes a stiff support on which the prefilter is mounted, said support being hydrophobic and non-absorbent.

8. A device according to claim 1, wherein said prefilter is an absorbent or filtering paper that includes glass fibers.

9. A device according to claim 3, wherein the density of the pores is such that said pores occupy 50% to 80% of the surface area of the membrane.

10. A device according to claim 1, wherein the device comprises a stiff support on which the prefilter is mounted, a peel-off adhesive which is peelable from the support, the prefilter, the membrane and the absorbent paper without tearing them away.

* * * * *

UNITED STATES PATENT AND TRADEMARK OFFICE
CERTIFICATE OF CORRECTION

PATENT NO. : 9,023,292 B2  
APPLICATION NO. : 12/740920  
DATED : May 5, 2015  
INVENTOR(S) : Rostaing et al.

Page 1 of 1

It is certified that error appears in the above-identified patent and that said Letters Patent is hereby corrected as shown below:

Title page,
Item (75) Inventors: "Gagna (FR)" should read --Gagny (FR)--.

Signed and Sealed this
Twelfth Day of January, 2016

Michelle K. Lee
*Director of the United States Patent and Trademark Office*